(12) United States Patent
Kotila

(10) Patent No.: US 8,425,431 B1
(45) Date of Patent: Apr. 23, 2013

(54) BLOOD SAMPLE OBTAINING DEVICE

(76) Inventor: Sylvana Kotila, Minneapolis, MN (US)

( * ) Notice: Subject to any disclaimer, the term of this patent is extended or adjusted under 35 U.S.C. 154(b) by 121 days.

(21) Appl. No.: 13/166,456

(22) Filed: Jun. 22, 2011

Related U.S. Application Data

(63) Continuation-in-part of application No. 12/037,865, filed on Feb. 26, 2008, now abandoned.

(60) Provisional application No. 60/891,585, filed on Feb. 26, 2007.

(51) Int. Cl.
*A61B 5/00* (2006.01)

(52) U.S. Cl.
USPC .......................... 600/573; 119/174; 600/584

(58) Field of Classification Search .................. 600/573, 600/576, 584; 606/116, 117, 181; 119/174, 119/655
See application file for complete search history.

(56) References Cited

U.S. PATENT DOCUMENTS

| 5,209,757 A | 5/1993 | Krug et al. |
| 6,343,223 B1 | 1/2002 | Chin et al. |

FOREIGN PATENT DOCUMENTS

SU 1209179 A 2/1986

*Primary Examiner* — Brian Szmal
*Assistant Examiner* — Emily Lloyd
(74) *Attorney, Agent, or Firm* — Dicke, Billig & Czaja, PLLC

(57) ABSTRACT

A blood sample obtaining device including a first arm, a second arm, a light source and a pressure applying head. The first arm and the second arm are operably connected to each other. The light source is mounted with respect to the first arm. The pressure applying head is mounted with respect to the second arm.

25 Claims, 2 Drawing Sheets

BLOOD SAMPLE OBTAINING DEVICE

REFERENCE TO RELATED APPLICATION

This application is a continuation-in-part and claims priority to U.S. application Ser. No. 12/037,865, filed Feb. 26, 2008. This application also claims priority to U.S. Application No. 60/891,585, filed Feb. 26, 2007, the details of which are incorporated herein by reference.

FIELD OF THE INVENTION

The invention relates generally to a system for obtaining blood samples. More particularly, the invention relates to a system for obtaining a blood sample from a feline or canine.

BACKGROUND OF THE INVENTION

Diabetes mellitus affects about 1 in 300 to 400 felines and a similar number in dogs. While each case is different, the monitoring of the animal's blood glucose remains equally important to ensure proper response from the animal to therapy. Monitoring can be used through the use of urine analysis strips but it is not nearly as accurate as that of a blood sample. It can also be difficult to obtain uncontaminated urine samples from cats and dogs.

One of the most challenging aspects of monitoring the glucose level using a blood sample is obtaining a blood sample from the animal. Because of the proximity of veins to the surface of the ear in felines and canines, the blood sample is typically obtained from the ear.

To retrieve the blood sample from the ear, it is necessary to determine the location of the vein or capillary bed. While it is known that veins on the cat's ear generally lie along the edge of the ear, illumination is typically necessary to ascertain the exact location of the veins.

The use of illumination thereby decreases the number of punctures needed to obtain the blood sample, which reduces bruising and possible damage to the ear that could impede the use of the ear for obtaining blood samples for future glucose tests.

Once the vein is located, a clamp is used as a tourniquet to put pressure on the vein and thereby allow for the vein to enlarge with ample blood. A lancet or puncturing device is used to puncture the skin and thereby obtain the blood sample.

Many people have a difficult time puncturing their pet's ear for fear of puncturing themselves at the same time, and not retrieving the blood sample on the first try thus having to puncture the ear numerous times. The illuminated clamp's lower arm may serve as a barrier to prevent the operator from puncturing themselves through the animal's ear and the illumination displays the vein to allow an operator to accurately puncture the vein on the first try.

Goryushins, Russian Patent No. 1209179, discloses a device having two pivotally mounted arms 3, 4 that may be used in conjunction with obtaining a blood sample. A first arm 3 includes a light source 12 that is used for illuminating the area from which it is desired to obtain the blood source. A second arm 4 includes a pressure applying head 1 with a slot 6 through which a needle (also identified with reference number 6) can be extended to puncture the skin.

The first arm 3 and the second arm 4 each include two rubber bands (also identified with reference number 6) that extend there over on opposite sides of where the skin is to be punctured. While not illustrated, it is envisioned that the rubber bands contact the opposite sides of the skin to prevent the skin from moving while the skin is punctured.

SUMMARY OF THE INVENTION

An embodiment of the invention is directed to a blood sample obtaining device having a first arm, a second arm, a light source and a pressure applying head. The first arm and the second arm are operably connected to each other. The light source is mounted with respect to the first arm. The pressure applying head is mounted with respect to the second arm.

Another embodiment of the invention is directed to a method for obtaining a blood sample. A blood sample obtaining device is provided. The blood sample obtaining device includes a first arm and a second arm that are operably connected to each other. A light source is mounted with respect to the first arm. A pressure applying head is mounted with respect to the second arm.

A portion of a body from which a blood sample is to be obtained is positioned between the first arm and the second arm. The light source illuminates the body to identify a location from which the blood sample will be obtained. The first arm and the second arm are moved to a closed configuration to retain the body in a substantially stationary position with respect to the first arm and the second arm. The body is punctured to obtain the blood sample.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE PREFERRED EMBODIMENTS

Figure 1:
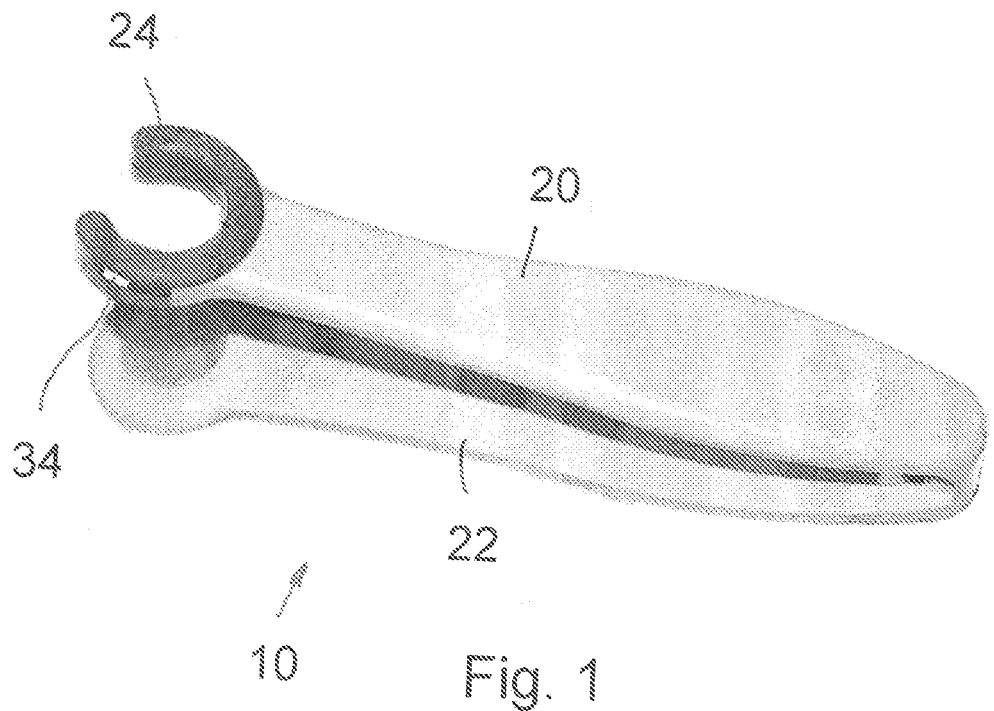
FIG. 1 is a perspective view of a blood sample obtaining device according to an embodiment of the invention.

An embodiment of the invention is directed to a blood sample obtaining device, as illustrated at 10 in the Figures. The blood sample obtaining device 10 enables a vein in a feline or canine's ear to be readily identified and then enables a blood sample to be obtained from the feline or canine.

While the invention is suitable for locating a blood source from a variety of animal body parts, it is particularly suitable for finding a blood source in feline and canine ears because of the relatively small thickness of the feline or canine ears as well as the proximity of veins to the surface of the ear. In certain embodiments, the blood sample obtaining device 10 is used for guiding an operator to a vein or capillary bed in the ear so that a blood sample can be obtained for glucose monitoring.

The blood sample obtaining device 10 generally includes an upper arm 20 and a lower arm 22 that are operably connected to each other. In certain embodiments, the upper arm 20 and the lower arm 22 may be pivotally attached to each other for movement between an open configuration and a closed configuration.

A distance between the distal ends of the upper arm 20 and the lower arm 22 when in the open configuration may be greater than a distance between the distal ends of the upper arm 20 and the lower arm 22 when in the closed configuration.

When the upper arm 20 and the lower arm 22 are in the open configuration, a distance between the distal ends of the upper arm 20 and the lower arm 22 is greater than a thickness of a portion of the feline or canine ear from which the blood sample is desired to be obtained. The distal end of the upper arm 20 and the lower arm 22 may thereby be placed over the portion of the feline or canine ear when the upper arm 20 and the lower arm 22 are in the open configuration.

When the upper arm 20 and the lower arm 22 are in the closed configuration, a distance between the distal ends of the upper arm 20 and the lower arm 22 is less than a thickness of the portion of the feline or canine ear from which the blood sample is desired to be obtained. The feline or canine ear is thereby retained in a stationary position with respect to the blood sample obtaining device 10 to facilitate obtaining the blood sample.

The upper arm 20 and the lower arm 22 may be maintained in the closed configuration by pressure from the user's hands. Alternatively or additionally, the upper arm 20 and the lower arm 22 may be maintained in the closed configuration with a locking mechanism (not shown). The locking mechanism may be adjustable such as to change the distance between the distal ends of the upper arm 20 and the lower arm 22 in the locked configuration.

The pressure exerted on the feline or canine ear by the upper arm 20 and the lower arm 22 is sufficiently large so that the blood sample obtaining device 10 resists movement with respect to the feline or canine ear and so that blood collects in an open region within a pressure applying head 24. However, the force should not be sufficiently large such that the animal experiences discomfort or injury.

In certain embodiments, the upper arm 20 and the lower arm 22 may be biased to the open configuration using a spring 38. An example of one such device that may be used to bias the upper arm 20 and the lower arm 22 to the open configuration is a spring operably attached to at least one of the upper arm 20 and the lower arm 22. In certain embodiments, the biasing force may be adjustable.

The upper arm 20 may include the pressure applying head 24 that is used in conjunction with positioning the blood sample obtaining device 10 with respect to the vein. In certain embodiments, the pressure applying head 24 may be constructed in a generally C-shape. The C-shape generally includes an open region and an enclosed region.

The open region does not apply force to the animal's ear so that blood may flow into the open region. The enclosed region may extend around an outer surface of the pressure applying head 24. When the upper arm 20 and the lower arm 22 are in the closed configuration, the enclosed region restricts the ability of blood to flow out of the ear through the portion of the ear that is contacted by the pressure applying head 24.

The pressure applying head 24 may be movably mounted with respect to the upper arm 20 to change the orientation of the pressure applying head 24 with respect to the upper arm 20. In certain embodiments, the pressure applying head 24 may be rotatably mounted to the upper arm 20.

Rotating of the pressure applying head 24 with respect to the upper arm 20 may be advantageous to allow the blood sample obtaining device 10 to be used with both of the animal's ears as well as for use at different locations on the animal's ears.

At least one guiding mark 26 may be provided on the pressure applying head 24. The guiding marks 26 may be useful for positioning a lancet operating device with respect to the vein and the blood sample obtaining device 10. Such a process may not be needed when a manual puncturing device is used in conjunction with the blood sample obtaining device 10.

Figure 4:
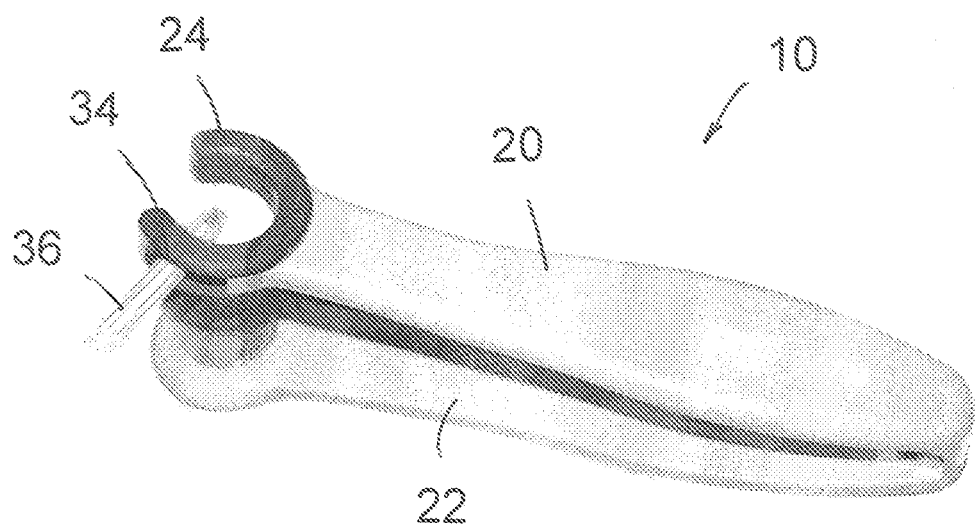
FIG. 4 is a perspective view of the blood sample obtaining device used in conjunction with a blood sample collection device.

The pressure applying head 24 may have at least one test strip slot 34 formed therein, as illustrated in FIG. 1. The test strip slot 34 may have a height and a width that are slightly larger than the height and the width of the test strip or other blood collection device 36 that is intended to be used with the blood sample obtaining device 10, as illustrated in FIG. 4.

The test strip 36 may resist sliding with respect to the pressure applying head 24 when the test strip 36 is positioned in the test strip slot 34. This configuration thereby enables the test strip 36 to be held in position proximate to where the ear is to be punctured so that the blood can be collected with the test strip 36 without the person using the blood sample obtaining system 10 having to hold the test strip 36 while using the blood sample obtaining device 10.

Figure 2:
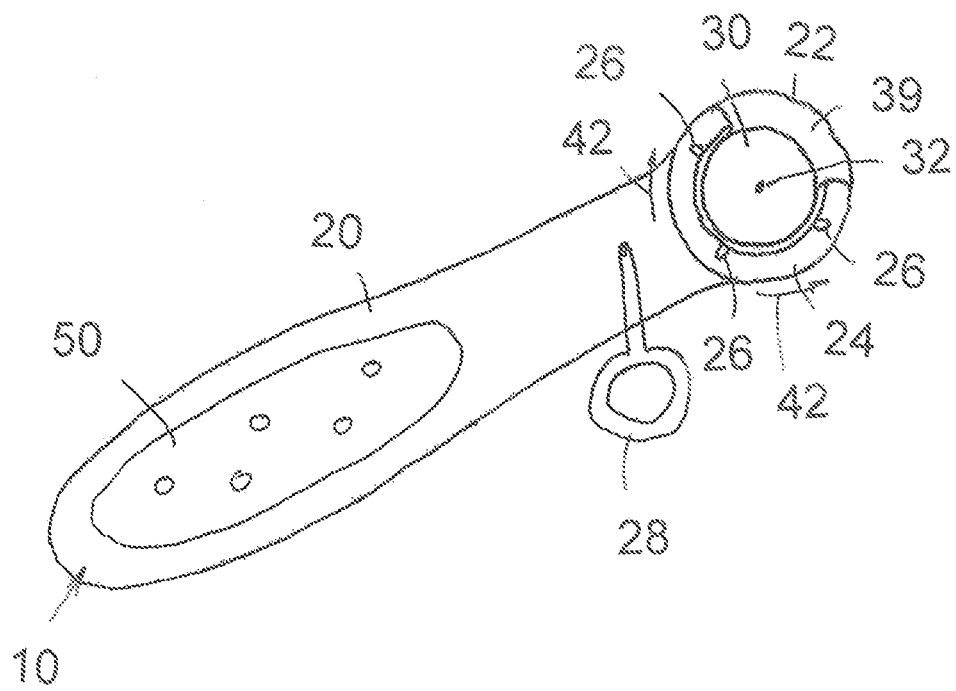
FIG. 2 is a top view of the blood sample obtaining device.
Figure 3:
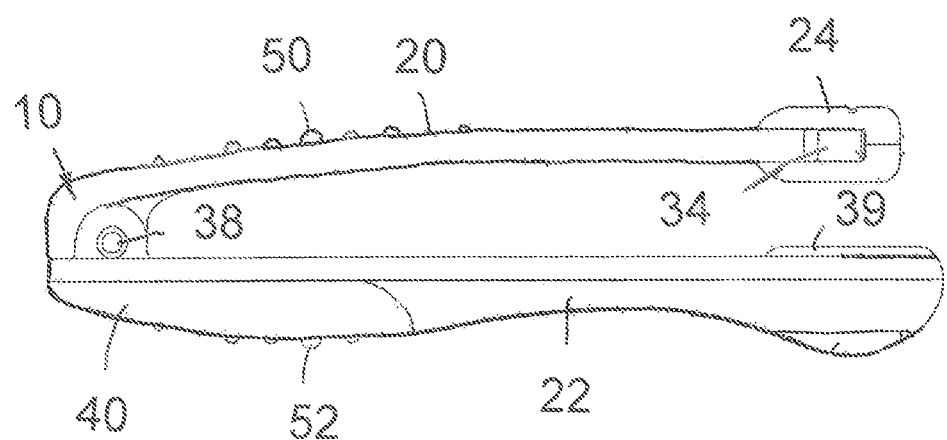
FIG. 3 is a side view of the blood sample obtaining device.

In certain embodiments, two of the guiding marks 26 may be positioned on arms of the C-shaped pressure applying head 24 so that these two guiding marks 26 are in a linear configuration, as illustrated in FIG. 2. Another guiding mark 26 may be provided intermediate the first two guiding marks 26. Each of the guiding marks 26 is thereby oriented at an angle of about 90 degrees from each other about a rotational axis of the C-shaped pressure applying head 24. The guiding marks 26 can be viewed as being located at about 3 o'clock, 6 o'clock and 9 o'clock on the surface of a conventional clock.

A lower surface of the pressure applying head 24 may be formed from a material that resists slipping of the pressure applying head 24 with respect to the ear when the upper arm 20 and the lower arm 22 are in the closed configuration.

To enhance the ability to accurately locate the vein or capillary bed, a magnifying means may be used in conjunction with the blood sample obtaining device 10. In certain embodiments, the magnifying means or lens 28 may be mounted on the upper arm 20.

The magnifying means 28 may be positioned on the upper arm 20 sufficiently far above the pressure applying head 24 so that the magnifying means 28 does not interfere with the use of the puncturing device such as lancet.

The magnification means 28 may be mounted such that if the user chooses not to use magnification means 28, the magnification means or lens 28 can be moved such as by pivoting laterally from access opening.

The lower arm 22 may include a lighting source 30 that is used for illuminating the vein or blood source in the animal's ear. The lighting source 30 may generally include a light 32 of suitable size including a LED bulb.

A protective covering 39 may be positioned over the light 32 to protect the light 32 from being damaged while the blood sample obtaining device is being used. The protective covering 39 may also serve as a protective barrier between the puncturing device and the operator to prevent the operator's skin from being punctured while using the blood sample obtaining device.

The light 32 may be powered using at least one battery (not shown) that is mounted with respect to the blood sample obtaining device 10. In certain embodiments, the at least one battery is positioned in a recess provided in the blood sample obtaining device 10 and the recess is at least partially covered with a battery cover 40. The battery cover 40 may be removably attached to the other portions of the blood sample obtaining device 10.

The blood sample obtaining device 10 may include a switch that is used for turning the light 32 on and off. In certain embodiments, the switch is automatically engaged when the upper arm 20 and the lower arm 22 are moved at least partially a distance between the open configuration and the closed configuration. Such a configuration enables the light to turn on before the upper arm 20 and the lower arm 22 are in the closed configuration.

In other embodiments, the switch may be activated and deactivated separately from the movement of the upper arm 20 and the lower arm 22. For example, a manually operable switch may be provided on at least one of the upper arm 20 and the lower arm 22.

In still other embodiments, the switch may be activated when the blood sample obtaining device 10 is moved from a stationary position. If the blood sample obtaining device 10 is not moved for a specified period of time that is greater than the period of time typically needed to obtain the blood sample, the switch may cause the light 32 to turn off. It is also possible to activate the light 32 by contact between at least one of the upper arm 20 and the lower arm 22 and the animal's ear.

To enhance the ability for a user to hold the blood sample obtaining device 10 and thereby reduce the potential of the operator's hand from slipping when holding the blood sample obtaining device 10, at least one of the upper arm 20 and the lower arm 22 may include a gripping enhancement mechanism.

In certain embodiments, the upper arm 20 may include an upper grip 50 on an outer surface thereof. Similarly, lower arm 22 may include a lower grip 52 on an outer surface thereof.

In operation, the blood sample obtaining device 10 is placed over the animal's ear (not shown). The upper arm 20 and the lower arm 22 are moved to a partially closed configuration to activate the light 32. The light 32 is used to locate a vein through the access opening in the pressure applying head 24.

Once the vein is located, the pressure applying head 24 is rotated as indicated by arrow 42 so pressure may be applied on one spot of the vein. The guiding marks 26 may also be positioned to facilitate accurately puncturing the vein. The upper arm 20 and the lower 12 are then moved to the closed configuration to retain the blood sample obtaining device 10 in a fixed position with respect to the animal's ear.

In certain circumstances, it may be desirable to wait a short period of time for blood to accumulate in the vein. In certain embodiments, the period of time is up to about 10 seconds. The operator may then puncture the site such as with a lancet, which allows blood to flow freely onto the animal's ear. Thereafter, a blood sample is collected with a glucose test strip or other blood collection device 36.

Once a sufficient quantity of blood has been collected, the operator releases the upper arm 20 and the lower arm 22 and removes the blood sample obtaining device 10 from the position over the animal's ear.

In the preceding Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A blood sample obtaining system comprising:
a blood sample obtaining device comprising:
 a first arm;
 a second arm that is operably connected to the first arm;
 a light source mounted to the first arm, wherein the light source is adapted to emit light; and
 a pressure applying head mounted to the second arm, wherein the pressure applying head has an open region formed therein and wherein the pressure applying head is rotatable with respect to the second arm, wherein the first arm and the second arm are configured to move to a closed configuration to retain a body portion in a stationary position with respect to the first arm and the second arm, and wherein the light source is configured to illuminate the body portion through the open region to aid a user in identifying a location for blood sampling; and
a puncturing device that is configured to puncture the body portion.

2. The blood sample obtaining system of claim 1, wherein the first and second arms are biased away from each other.

3. The blood sample obtaining system of claim 2, wherein a biasing force is adjustable.

4. The blood sample obtaining system of claim 1, and further comprising a protective cover mounted at least partially over the light source, wherein the light is visible through the protective cover.

5. The blood sample obtaining system of claim 1, wherein the light source is configured to be activated using a technique selected from the group consisting of when the first arm and the second arm are moved from an open configuration toward a closed configuration, by movement of at least one of the first arm and the second arm from a stationary position, by an on/off switch or combination thereof.

6. The blood sample obtaining system of claim 1, wherein the open region on the pressure applying head is configured to allow blood to flow into a puncture site.

7. The blood sample obtaining system of claim 1, wherein the pressure applying head is capable for use as a guide for a puncture site.

8. The blood sample obtaining system of claim 1, and further comprising at least one guiding mark on the pressure applying head.

9. The blood sample obtaining system of claim 1, and further comprising a magnifying means operably connected to at least one of the first arm and the second arm.

10. The blood sample obtaining system of claim 9, wherein the magnifying means is movable between a use position and a storage position.

11. The blood sample obtaining system of claim 1, and further comprising a battery mounted with respect to at least one of the first arm and the second arm, wherein the battery is operably connected to the light source.

12. The blood sample obtaining system of claim 1, wherein rotation of the pressure applying head with respect to the second arm is configured to change an orientation of the open region with respect to the second arm.

13. The blood sample obtaining system of claim 1, wherein the pressure applying head further comprises a slot formed therein and wherein the slot is configured to receive a blood collection device.

14. A method for obtaining a blood sample comprising:
providing a blood sample obtaining device comprising a first arm and a second arm that are operably connected to each other, a light source mounted to the first arm, and a pressure applying head rotatably mounted to the second arm, wherein the light source is adapted to emit light and wherein the pressure applying head has an open region formed therein through which the light may be viewed;
positioning a portion of a body from which a blood sample is to be obtained between the first arm and the second arm;
illuminating the body with the light to identify a location from which the blood sample will be obtained;
moving the first arm and the second arm to a closed configuration to retain the body in a stationary position with respect to the first arm and the second arm; and
puncturing the body to obtain the blood sample.

15. The method of claim 14, and further comprising providing at least one guide mark on the pressure applying head to identify a location from which the blood sample is to be obtained.

16. The method of claim 14, and further comprising providing a magnifying means on the second arm to facilitate identifying a location from which the blood sample is to be obtained.

17. The method of claim 14, and further comprising biasing the first arm and the second arm away from each other.

18. The method of claim 14, wherein the light source is activated using a technique selected from the group consisting of when the first arm and the second arm are in a closed configuration, by contact with an ear, by movement of the first arm and the second arm from a stationary position, by an on/off switch or combination thereof.

19. The method of claim 14, wherein the pressure applying head comprises only one point for compression thus allowing blood flow into a puncture site.

20. The method of claim 14, and further comprising mounting a battery with respect to at least one of the first arm and the second arm and operably connecting the battery to the light source.

21. The method of claim 14, wherein rotation of the pressure applying head with respect to the second arm changes an orientation of the open region with respect to the second arm.

22. The method of claim 14, and further comprising rotating the pressure applying head with respect to the second arm.

23. The method of claim 14, and further comprising:
providing a blood collection device;
providing a slot in the pressure applying head;
extending the blood collection device through the slot, wherein the slot is configured to hold the blood collection device in a stationary position with respect to the pressure applying head; and
collecting the blood sample with the blood collection device.

24. A blood sample obtaining system comprising:
a tissue stabilization device comprising:
a first arm;
a second arm that is operably connected to the first arm;
a light source mounted to the first arm, wherein the light source is adapted to emit light; and
a pressure applying head mounted to the second arm, wherein the pressure applying head has an open region formed therein, wherein the pressure applying head is rotatable with respect to the second arm, wherein the pressure applying head further comprises a slot, wherein the first arm and the second arm are configured to move to a closed configuration to retain a body portion in a stationary position with respect to the first arm and the second arm, and wherein the light source is configured to illuminate the body portion through the open region to aid a user in identifying a location for blood sampling; and
a blood collection device configured to be placed through the slot.

25. The blood sample obtaining system of claim 24, wherein the slot is configured to hold the blood collection device.

\* \* \* \* \*